United States Patent
Cho et al.

(10) Patent No.: US 7,387,965 B2
(45) Date of Patent: Jun. 17, 2008

(54) REFERENCE PATTERN FOR CREATING A DEFECT RECOGNITION LEVEL, METHOD OF FABRICATING THE SAME AND METHOD OF INSPECTING DEFECTS USING THE SAME

(75) Inventors: Won-Il Cho, Yongin-si (KR); In-Kyun Shin, Yongin-si (KR); Jin-Hyung Park, Seongnam-si (KR)

(73) Assignee: Samsung Electronics Co, Ltd., Suwon-Si (KR)

( * ) Notice: Subject to any disclaimer, the term of this patent is extended or adjusted under 35 U.S.C. 154(b) by 76 days.

(21) Appl. No.: 10/848,250

(22) Filed: May 18, 2004

(65) Prior Publication Data
US 2005/0009355 A1 Jan. 13, 2005

(30) Foreign Application Priority Data
Jul. 8, 2003 (KR) ...................... 10-2003-0046181

(51) Int. Cl.
*H01L 21/311* (2006.01)
(52) U.S. Cl. ...................................... 438/694; 356/237
(58) Field of Classification Search ................ 438/694; 356/237
See application file for complete search history.

(56) References Cited

U.S. PATENT DOCUMENTS

| 4,357,540 A | * | 11/1982 | Benjamin et al. ......... 250/491.1 |
| 5,076,692 A | * | 12/1991 | Neukermans et al. ....... 356/338 |
| 6,028,953 A | * | 2/2000 | Nakamura et al. .......... 382/144 |
| 6,096,656 A | * | 8/2000 | Matzke et al. .............. 438/702 |
| 6,411,378 B1 | | 6/2002 | Pike |
| 6,428,938 B1 | * | 8/2002 | Lin et al. ........................ 430/5 |
| 2003/0030796 A1 | * | 2/2003 | Nakanishi ................ 356/237.5 |

FOREIGN PATENT DOCUMENTS

| JP | 2002-055435 | * | 2/2002 |
| KR | 10-1998-021216 | | 6/1998 |
| KR | 100161593 | | 8/1998 |
| KR | 10-1999-018381 | | 3/1999 |
| KR | 0141496 | | 8/1999 |
| KR | 1020020025844 | | 4/2002 |
| KR | 1020020096682 | | 12/2002 |

* cited by examiner

*Primary Examiner*—Shamim Ahmed
*Assistant Examiner*—Mahmoud Dahimene
(74) *Attorney, Agent, or Firm*—F. Chau & Associates, LLC (57) ABSTRACT

A reference pattern for creating a defect recognition level comprises a blank region formed on a transparent substrate and a grating region formed adjacent to the blank region, wherein the grating region includes a plurality of parallel trench lines.

32 Claims, 11 Drawing Sheets

FIG. 1A

Prior Art

FIG. 1B

Prior Art

FIG. 1C

Prior Art

FIG. 1D

Prior Art

REFERENCE PATTERN FOR CREATING A DEFECT RECOGNITION LEVEL, METHOD OF FABRICATING THE SAME AND METHOD OF INSPECTING DEFECTS USING THE SAME

CROSS-REFERENCE TO RELATED APPLICATION

This application claims priority to Korean Patent Application No. 2003-46181, filed on Jul. 8, 2003, which is incorporated herein by reference in its entirety.

BACKGROUND

1. Technical Field

The present disclosure relates to a photomask used in a process for manufacturing semiconductor devices, and more particularly, to a photomask having a reference pattern for creating a defect recognition level.

2. Discussion of Related Art

A photomask is a high precision plate containing patterns, i.e., microscopic images of electronic circuits. The photomask is used in wafer fabrication, mostly to make Integrated Circuits (ICs). Photolithography involves projecting photomask patterns onto a wafer. A defect is any flaw affecting the patterns on the photomask. Generally, defects on the photomask create errors to the ICs. The errors to the ICs may cause failures of a semiconductor device. Therefore, there exists a need to inspect the defects of the photomask during manufacturing semiconductor devices.

Conventionally, when inspecting for defects, a pattern being inspected is compared to a pattern on a database. With this inspection method, an image seen through a known inspecting device is compared to a digitalized image on the database. In other words, inspection results, obtained by detecting light-shielding patterns on the photomask, are compared to a reference data on the database. Another conventional inspection method is to compare two identical patterns after forming the two identical patterns on one photomask to determine if there is any discrepancy. The inspection results are also used to compare the two identical patterns. In the conventional inspecting methods, it is known that a defect recognition level is used to obtain the inspection results.

Figure 1A:
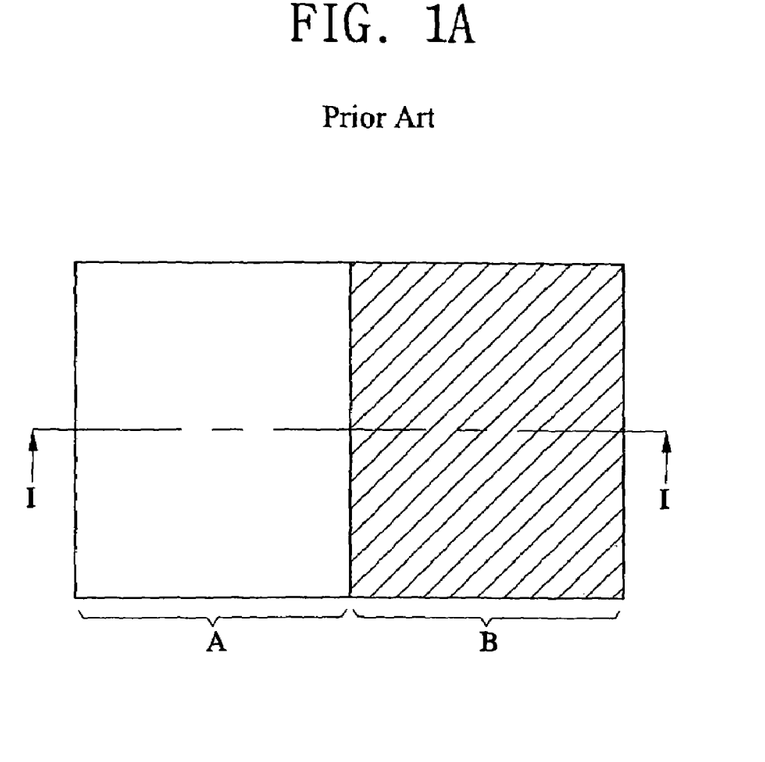
FIGS. 1a and 1b are a plain view and a cross-sectional view, respectively, showing a conventional reference pattern for creating a defect recognition level.
Figure 1B:
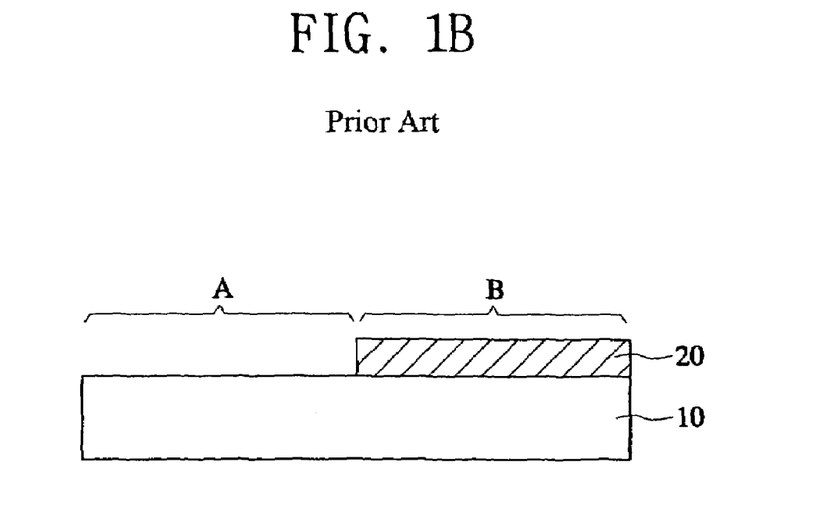

FIG. 1A is a plain view showing a reference pattern for creating a conventional defect recognition level. FIG. 1B is a cross-sectional view taken along the line I-I shown in FIG. 1A. Referring to FIGS. 1A and 1B, a conventional reference pattern includes a blank region A in which a transparent substrate 10 is exposed, and a light-shielding region B in which a light-shielding layer 20 is formed on the transparent substrate 10. The light-shielding region B is formed adjacent to the blank region A.

Figure 1C:
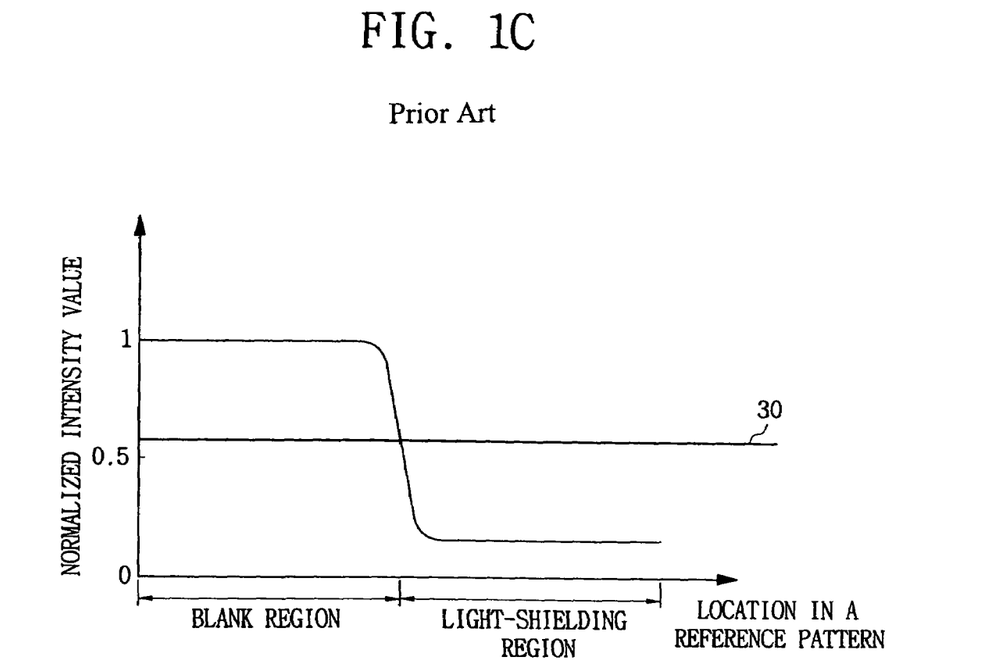
FIG. 1C is a graph showing a defect recognition level of a conventional reference pattern.

FIG. 1C is a graph showing a defect recognition level obtained by using the conventional reference pattern. Referring to FIG. 1C, light (not shown) is irradiated on an area including the blank region A and the light-shielding region B shown in FIG. 1A. Then, intensities of light transmitted to the blank region A and the light-shielding region B are measured by a known device. Most of the light is transmitted through the blank region A. The intensity of the light transmitted to the light-shielding region B is lower than the intensity of light transmitted to the blank region A because most of light irradiated on the light-shielding region B is blocked by the light-shielding layer 20.

Then, as shown in the graph of FIG. 1C, the intensity of the light transmitted to the blank region A, and the intensity of the light transmitted to the light-shielding region B can be indicated by normalized intensity values, respectively. For example, the intensity of the light transmitted to the blank region A is determined as a standard intensity value "1". The intensity of the light transmitted to the light-shielding region B can be represented as a relative value to the standard intensity value "1". A middle value between the standard intensity value "1" and the normalized intensity value of the light transmitted to the light shielding region B is determined as a defect recognition level 30.

After the defect recognition level 30 is determined, light is irradiated on an inspection pattern (for example, a pattern shown in FIG. 1D) of a photomask which is to be inspected. Then, intensities of light transmitted to the inspection pattern are measured by a known device. If a normalized intensity value of the light transmitted to the inspection pattern is lower than the defect recognition level 30, it is recognized that a light-shielding pattern exists on the transparent substrate.

Figure 1D:
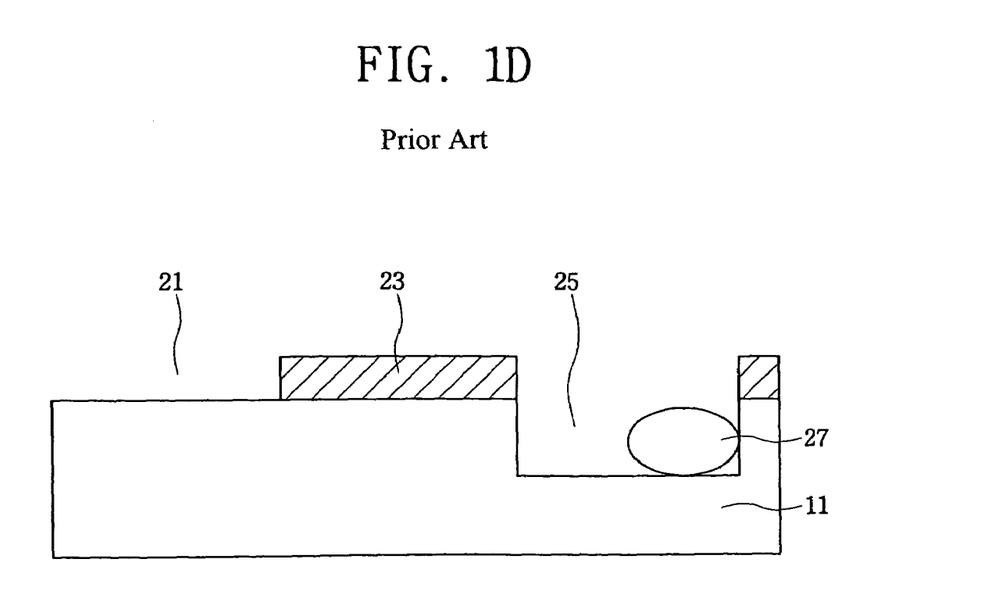
FIG. 1D is a cross-sectional view showing an inspection pattern of an alternating phase shift photomask.

FIG. 1D is a cross-sectional view of an inspection pattern of an alternating phase shift photomask under a defect inspection. Referring to FIG. 1D, the alternating phase shift photomask 400 includes a phase 0 degree region 21, a light-shielding region 23, and a phase shift region 25. A transparent substrate 11 is exposed in the phase 0 degree region 21. The transparent substrate 11 is covered with a light-shielding layer 22 in the light-shielding region 23. The transparent substrate 11 is etched to form the phase shift region 25. The phase 0 degree region, the light-shielding region 23, and the phase shift region 25 can alternately be aligned. For example, in a Cr-less mask (CLM), the phase 0 degree region 21 and the phase shift region 25 are alternately aligned because the CLM does not include a light-shielding layer 23.

When the transparent substrate 11 is etched to form the phase shift region 25, a transparent defect 27 can be formed in the phase shift region 25. Generally, because the transparent defect 27 (which was a part of the transparent substrate) is formed of the same material as the transparent substrate 11, the transmittance of the transparent defect 27 is same as the transmittance of the transparent substrate 11.

Figure 1E:
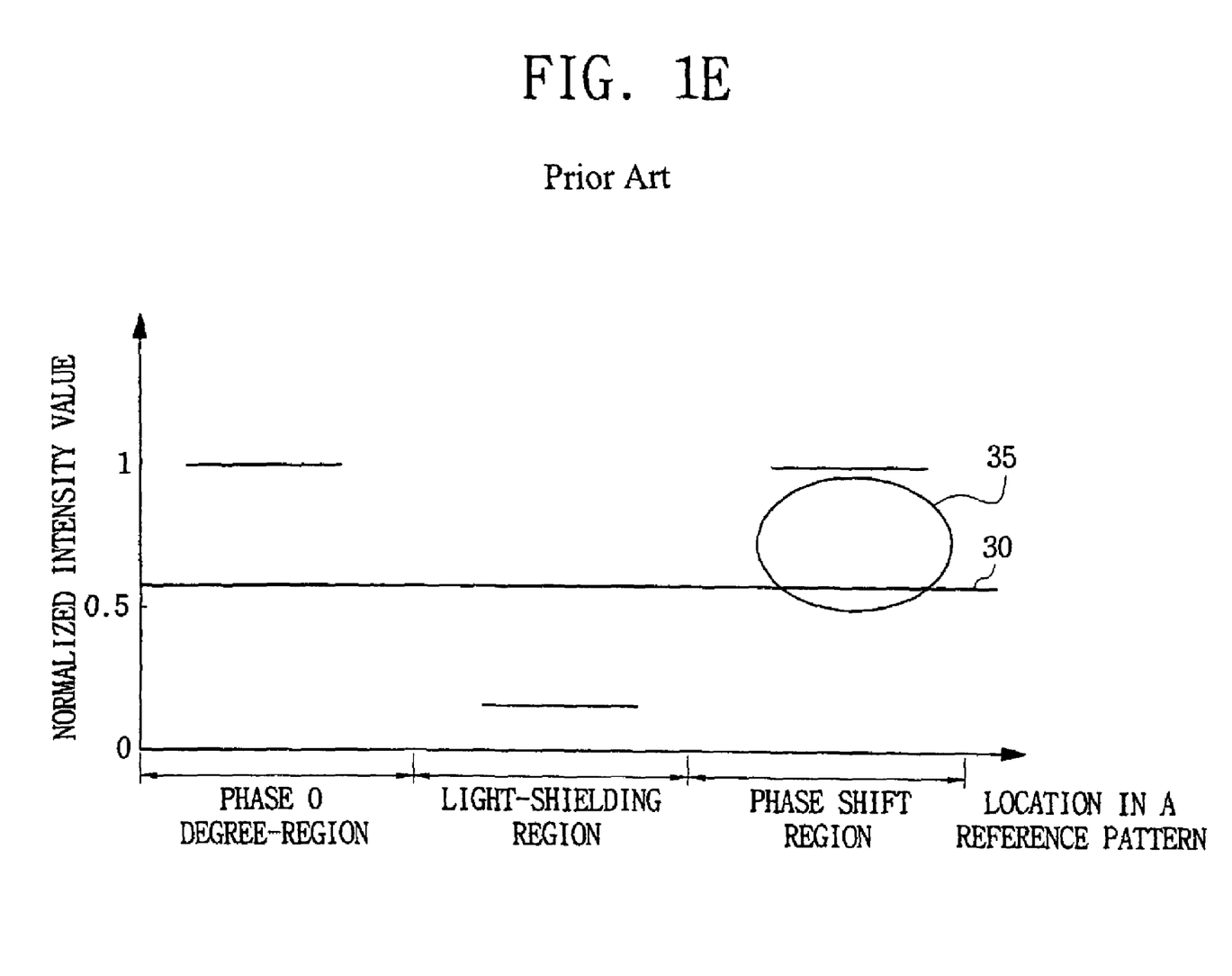
FIG. 1E is a graph showing a relationship between a conventional defect recognition level and normalized intensities of light transmitted to an inspection pattern.

FIG. 1E is a graph showing a relationship between the defect recognition level 30 and normalized intensity values of light transmitted to the inspection pattern of an alternating phase shift photomask 400 (shown in FIG. 1D). Referring to FIG. 1E, after determining the defect recognition level 30, light (not shown) is irradiated on the inspection pattern of the phase shift photomask 400 under the defect inspection. Then, intensities of the light transmitted to the inspection pattern are measured by a known device. When the normalized intensity value of light is close to "1", it is recognized that there is no light-shielding pattern (for example, the light shielding pattern 22 shown in FIG. 1D).

When the normalized intensity value of light is close to "0", it is recognized that there exists a light-shielding pattern. Because most of light can be transmitted through the transparent defect 27, the normalized intensity value of light transmitted to the transparent defect 27 is close to "1". However, the light transmitted to the phase shift region 25 and the light transmitted to the transparent defect 27 interfere with each other so that the normalized intensity value of light measured at a boundary of the transparent defect 27 and the phase shift region 25 is lower than "1".

The intensity of the light measured at the boundary of the transparent defect 27 and the phase shift region 25 varies depending on a phase angle of the light transmitted to the transparent defect 27. The intensity of the light provides various values of a defect distribution 35 depending on thickness of the transparent defect 27.

The lowest normalized intensity value of light in the defect distribution 35 can be obtained when the intensity of the light transmitted to the transparent defect 27 and the intensity of the light transmitted to the phase shift region 25 have 180 degrees of phase difference.

Even the lowest normalized intensity value in the defect distribution 35 can have a higher normalized intensity value than the normalized intensity value of the light measured at the light-shielding region 23 due to a limitation of a known inspection device. Because the intensity of light measured by the known inspection device is based on a given area, it is difficult to measure the intensity of light at the boundary of the transparent defect 27 and the phase shift region 25. As a result, when measuring the intensity of the light at the transparent defect 27 and the phase shift region 25, an intensity of light transmitted to adjacent areas can be included. Therefore, most of the values of the defect distribution 35 caused by the transparent defect 27 are located above the defect recognition level 30. As a result, most of the transparent defects 27 cannot be detected by the conventional defect recognition level 30.

SUMMARY OF THE INVENTION

Exemplary embodiments of the invention generally include reference patterns for creating defect recognition levels. In one exemplary embodiment, a reference pattern comprises a blank region formed on a transparent substrate and a grating region formed adjacent to the blank region, wherein the grating region includes a plurality of parallel trench lines.

In another exemplary embodiment, a method of forming a reference pattern comprises: forming a light-shielding layer on a transparent substrate; patterning the light-shielding layer to form a first light-shielding pattern and a second light-shielding pattern adjacent to the first light-shielding pattern, the first light-shielding pattern being formed of a single pattern covering the overall surface of a portion of the transparent substrate, and the second light-shielding pattern being formed of a plurality of parallel line patterns to form line-shaped openings exposing the transparent substrate; etching the transparent substrate using the first and the second light-shielding patterns as an etch mask to form trench lines corresponding to the line-shaped openings; and removing the first and the second light-shielding patterns to form a blank region corresponding to the first light-shielding pattern, and a grating region corresponding to the second light-shielding pattern.

In another exemplary embodiment, a method of creating a defect recognition level comprises: fabricating a reference pattern on a transparent substrate, the reference pattern including a blank region and a grating region formed adjacent to the blank region, wherein the grating region includes a plurality of trench lines formed in the transparent substrate; irradiating light on the reference pattern; measuring intensities of light transmitted to the reference pattern; and selecting a level between intensity of light transmitted to the blank region of the reference pattern and intensity of light transmitted to the grating region of the reference pattern.

In yet another exemplary embodiment of the invention, a method of inspecting defects comprises: fabricating a reference pattern on a transparent substrate, the reference pattern including a blank region on the transparent substrate, and a grating region formed adjacent to the blank region and having a plurality of trench lines formed in the grating region; irradiating light on the reference pattern; measuring intensities of light transmitted to the reference pattern; selecting a level between the intensity of light transmitted to the blank region of the reference pattern and the intensity of light transmitted to the grating region of the reference pattern; irradiating light on an inspection pattern under a defect inspection; measuring intensities of light transmitted to the inspection pattern; and reading the measured intensities of light and determining a presence or an absence of defects.

These and other exemplary embodiments, aspects, features and advantages of the present invention will become apparent from the following detailed description of exemplary embodiments, which is to be read in connection with the accompanying drawings.

DESCRIPTION OF EXEMPLARY EMBODIMENTS

Exemplary embodiments of the present invention will now be described more fully hereinafter below with reference to the accompanying drawings. This invention may, however, be embodied in different forms and should not be construed as limited to the exemplary embodiments set forth herein. Rather, these exemplary embodiments are provided so that this disclosure will be thorough and complete, and will fully convey the scope of the invention to those skilled in the art.

Figure 2A:
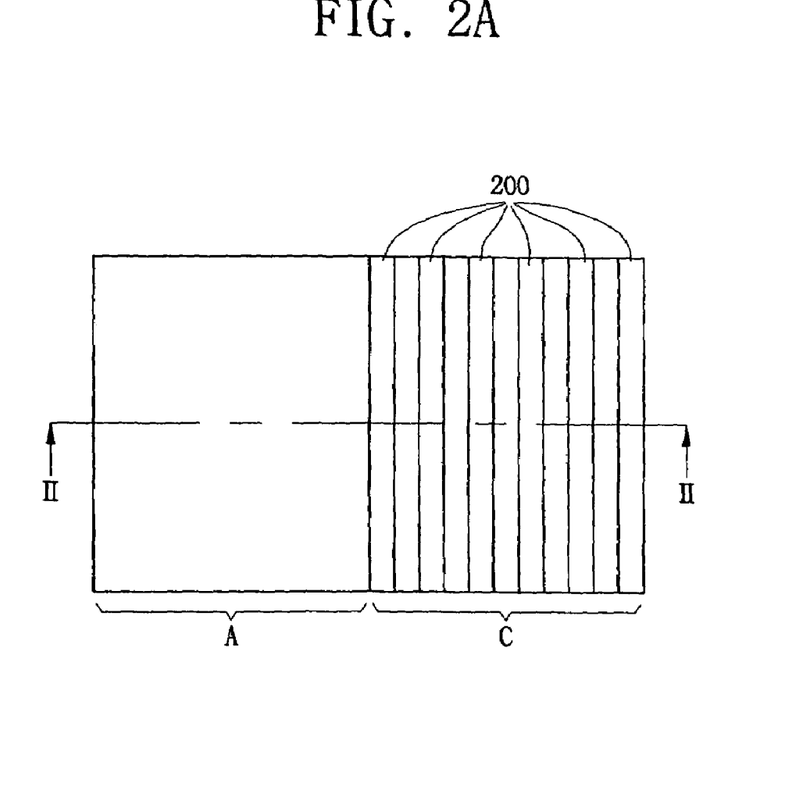
FIGS. 2A and 2B are a plain view and a cross-sectional view, respectively, showing a reference pattern for creating a defect recognition level according to an exemplary embodiment of the present invention.
Figure 2B:
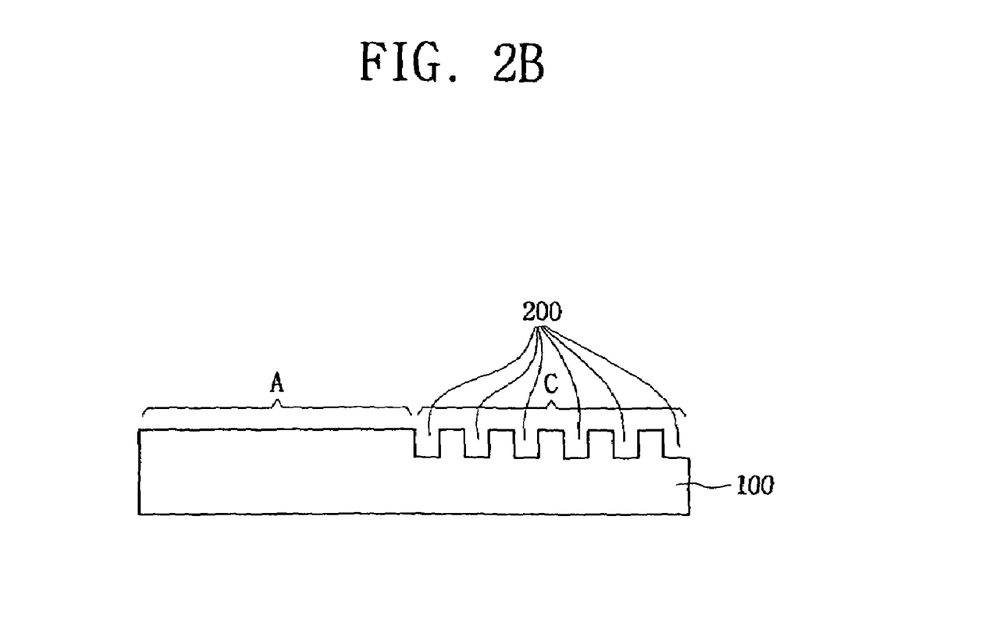

FIG. 2A is a plain view showing a reference pattern for creating a defect recognition level according to an exemplary embodiment of the present invention. FIG. 2B is a cross-sectional view taken along the line II-II shown in FIG. 2A. Referring to FIGS. 2A and 2B, the reference pattern according to an exemplary embodiment of the present invention includes a blank region A and a grating region C. A transparent substrate 100 is exposed in the blank region A. The grating region C is formed adjacent to the blank region A. The grating region C includes a plurality of trench lines 200. At least one of extension lines of the plurality of parallel trench lines 200 can cross the blank region A.

In one exemplary embodiment, the trench lines 200 may be parallel with the blank region A. The trench lines 200 may be formed to have an identical width and depth. Distances between two neighboring trench lines 200 may be formed to be identical. The trench lines 200 may be formed to have a depth and a width such that light transmitted to the blank region A has 180 degrees of phase difference with respect to light transmitted to the trench lines 200 during a defect inspection. The width of the trench lines 200 may be identical to the distance between two neighboring trench lines 200. The width of trench lines 200 and the distance between two neighboring trench lines 200 may have a small value so that intensities of light transmitted to the grating region C can maintain a constant value. The width of the trench lines and the distance between the two neighboring trench lines 200 may be less than about 300 nm.

The blank region A and the grating region C have at least a minimum size of area so that light transmitted to the blank region A and light transmitted to the grating region C are not affected by the interference of light transmitted to other regions (not shown) adjacent to the blank region A and the grating region C. Minimum size of the blank region A and the grating region C can be determined by, for example, the minimum size of area that is required to measure the amount of transmitted light in a known measuring device.

Figure 2C:
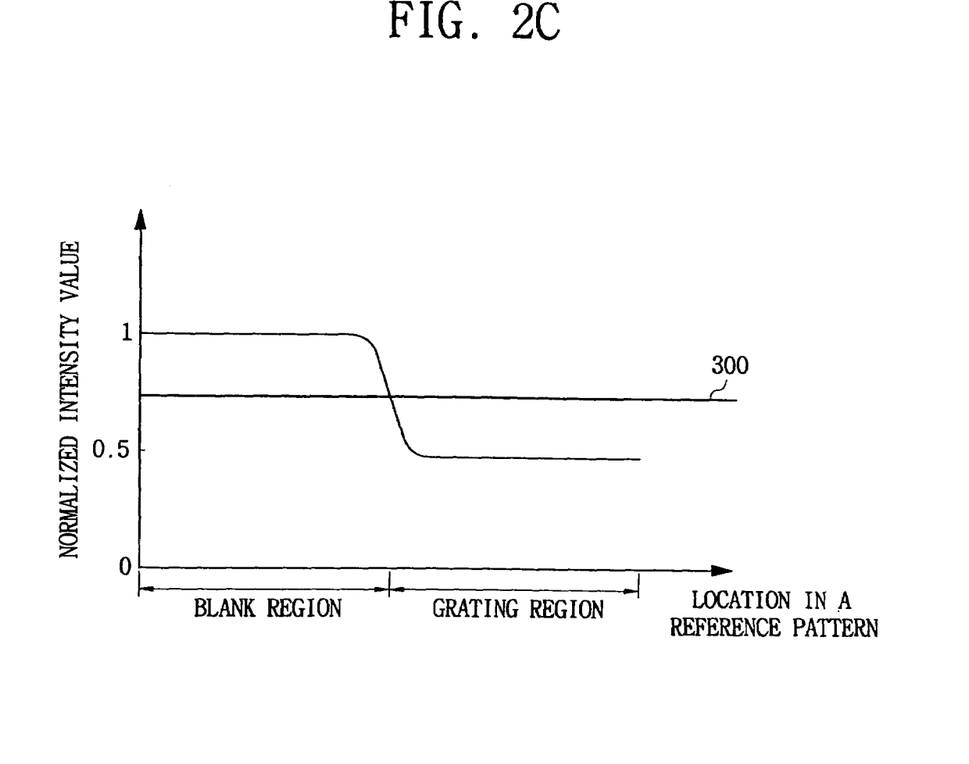
FIG. 2C is a graph showing a defect recognition level of a reference pattern according to an exemplary embodiment of the present invention.

FIG. 2C is a graph showing a defect recognition level 300 of a reference pattern according to an exemplary embodiment of the present invention. Referring to FIG. 2C, light is irradiated on a reference pattern including the blank region A and the grating region C shown in FIG. 2B, and then intensities of light transmitted to the area are measured. Intensity of light transmitted to the blank region A is higher than intensity of light transmitted to the grating region C since most of the light irradiated on the blank region A are transmitted through the blank region A, and there may be no interference between lights transmitted to the blank region A. The intensity of light transmitted to the blank region A is determined as the standard intensity value of "1".

The intensity of light transmitted to the grating region C is lower than the intensity of light transmitted to the blank region A since the light transmitted to the trench lines 200 shown in FIG. 2B and the light transmitted to the transparent substrate between the trench lines 200 interfere with each other. The intensity of light transmitted to the grating region C is normalized against standard value "1" being the intensity of light transmitted to the blank region A.

A value between the normalized intensity value of light transmitted to the grating region C and the standard intensity value "1" of light transmitted to the blank region A is determined as a defect recognition level 300. Generally, a middle value between the standard intensity value "1" of light transmitted to the blank region A and the intensity of light transmitted to the grating region C may be determined as the defect recognition level 300.

The intensity of light transmitted to the grating region C is lower than the intensity of light transmitted to the blank region A due to the interference of light. The intensity of light transmitted to the grating region C is higher than the intensity of light measured at the light-shielding region B shown in FIG. 1A, which shows a conventional reference pattern. Therefore, the defect recognition level 300 according to an exemplary embodiment of the present invention has a higher normalized intensity value than the conventional defect recognition level 30 shown in FIG. 1C.

Figure 2D:
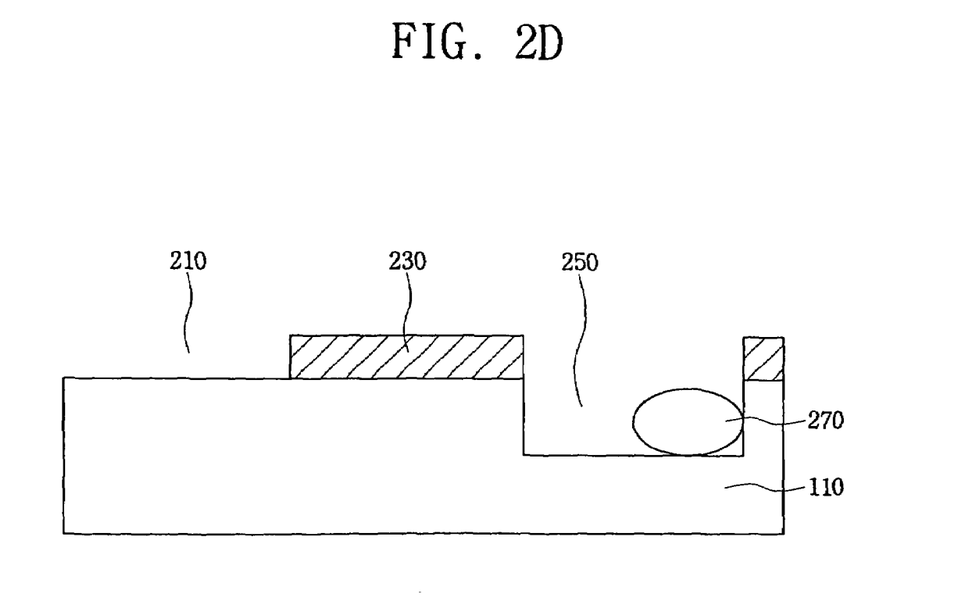
FIG. 2D is a cross-sectional view showing a defect inspection pattern of an alternating phase shift photomask.

FIG. 2D is a cross-sectional view showing an inspection pattern of an alternating phase shift photomask under a defect inspection. Referring to FIG. 2D and FIG. 1D, the alternating phase shift photomask 500 is configured to include a phase 0 degree region 210 in which a transparent substrate 110 is exposed, a light-shielding region 230, and a phase shift region 250. The phase 0 degree region 210, the light-shielding region 230, and the phase shift region 250 are alternately aligned. As described referring to FIG. 1D, the transparent substrate 110 is etched to form the phase shift region 250.

As a result of etching the transparent substrate 110, the phase shift region 250 may include a transparent defect 270 thereon. In other words, generally, the transparent defect 270 is generated when the transparent substrate 110 is etched. After an etching process, the transparent defect 270 may be a part of the transparent substrate 110 and remain in the photomask 500 because the transparent defect 270 is not cleansed completely. After the etching process, the transparent defect 270 may also be a part of the transparent substrate 110 because the transparent substrate 110 is not etched completely. The transparent defect 270 is formed of the same material as the transparent substrate 110 and the transmittance of the transparent defect 270 is same as the transmittance of the transparent substrate 110.

Figure 2E:
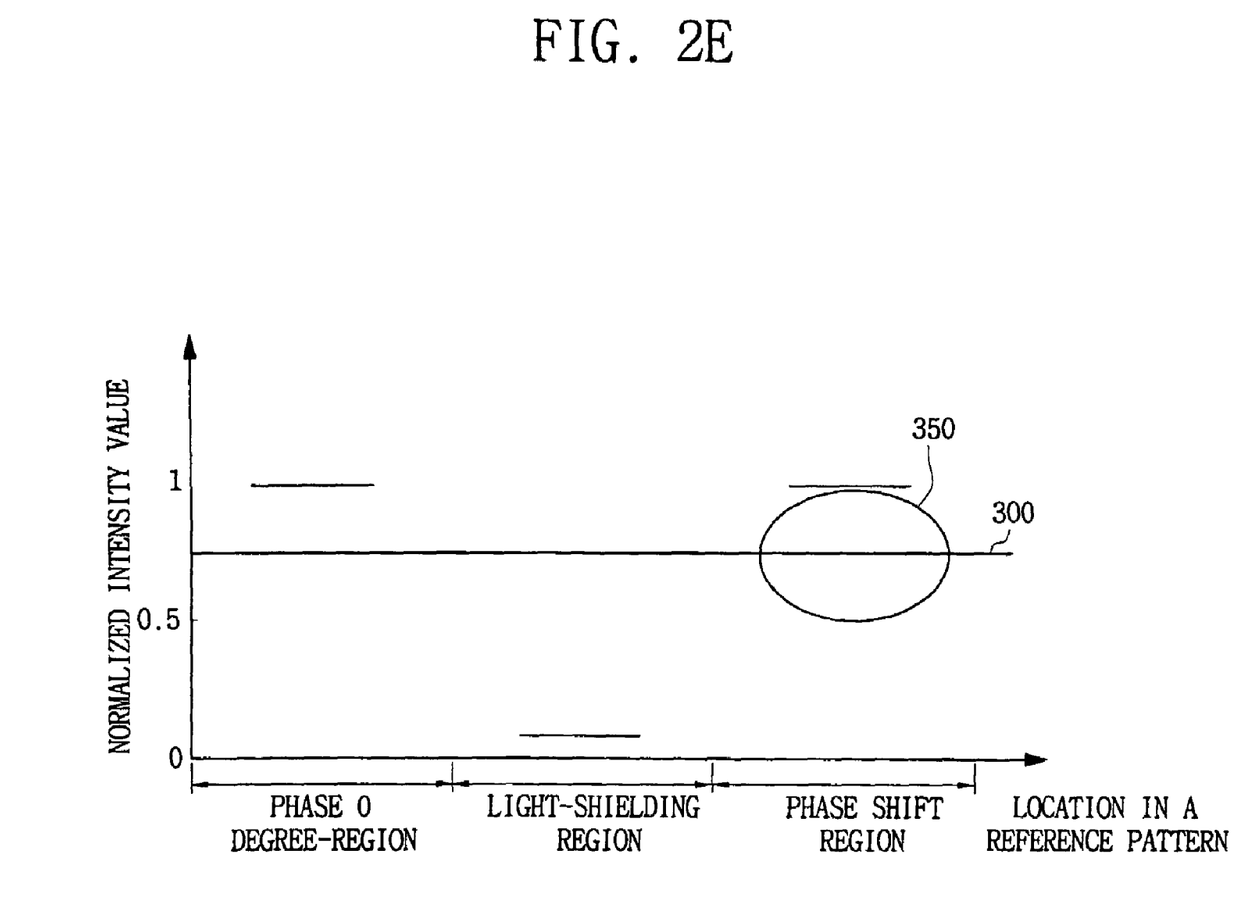
FIG. 2E is a graph showing a relationship between a defect recognition level according to an exemplary embodiment of the present invention and intensities of light transmitted to a defect inspection pattern of a photomask.

FIG. 2E is a graph showing a relationship between the defect recognition level 300 according to an exemplary embodiment of the present invention and the normalized intensity value of light transmitted to an inspection pattern of a photomask 500 under a defect inspection.

Referring to FIG. 2E, light is irradiated on the photomask 500 having the inspection pattern shown in FIG. 2D to measure intensities of light transmitted to the inspection pattern. The normalized intensity of light transmitted to the phase 0 degree region 210 is close to "1" since the phase 0 degree region 210 is rarely affected by light interference. The intensity of light transmitted to the light-shielding region 230 is close to "0" since most of the transmission of light to the light-shielding region 230 is blocked by the light shielding region 230. The phase shift region 250 shows an intensity of light identical to the intensity of light of the phase 0 degree region 210.

However, if the transparent defect 270 exists in the phase shift region 250, the intensity of light measured at a boundary of the transparent defect 270 and the phase shift region 250 is lower than the intensity of light transmitted to the phase shift region 250. The interference occurs between light transmitted to the transparent defect 270 and light transmitted to a portion of the phase shift region 250 adjacent to the transparent defect 270.

The intensity of light measured at the boundary of the transparent defect 270 and the phase shift region 250 may show various values of a defect distribution 350 due to the thickness of the transparent defect 270. As shown in FIG. 1E, some of the defect distribution 350 have a higher normalized intensity value than the defect recognition level 300 due to the limitation of a known inspection device.

However, the defect recognition level 300 according to an exemplary embodiment of the present invention shows a higher normalized intensity value of light than the conventional defect recognition level 30. Therefore, more transparent defects in the defect distribution 350 can be detected using the defect recognition level 300 than using the conventional defect recognition level 30.

Figure 3A:
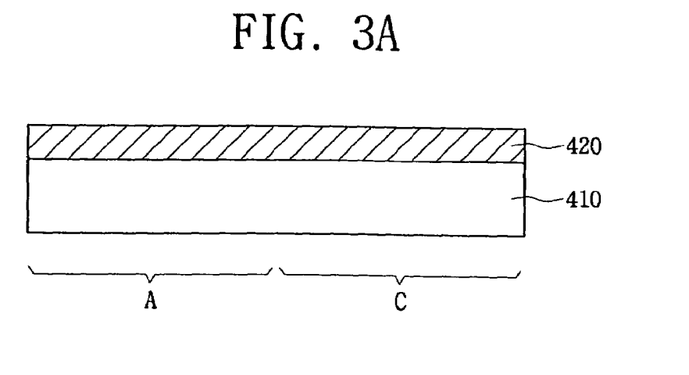
FIGS. 3A to 3C are cross-sectional views showing a method of forming a reference pattern for creating a defect recognition level according to an exemplary embodiment of the present invention.
Figure 3B:
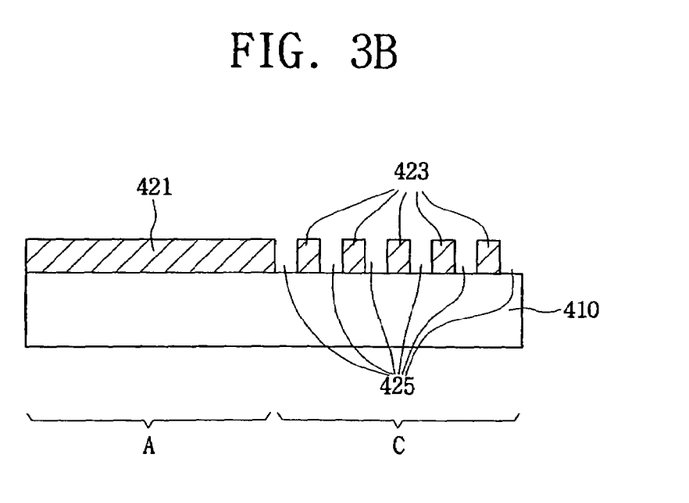
Figure 3C:
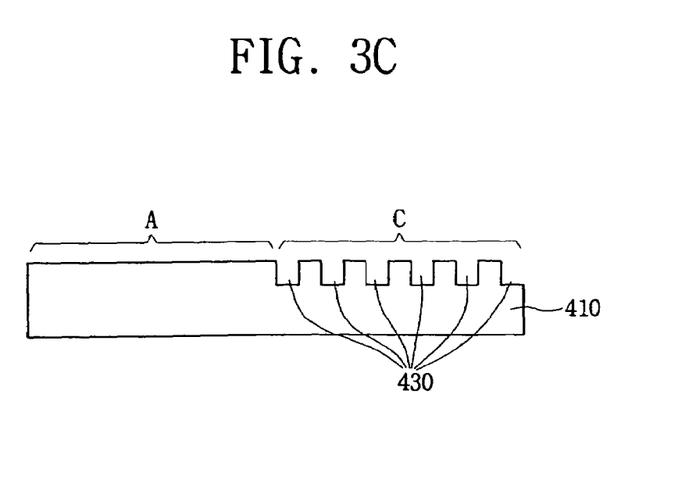

FIGS. 3A to 3C are cross-sectional views showing a method of forming a reference pattern for creating a defect recognition level according to an embodiment of the present invention.

Referring to FIG. 3A, a transparent substrate 410 includes a blank region A and a grating region C. Generally, quartz is used for the transparent substrate 410. A light-shielding layer 420 is formed on the transparent substrate 410. The light-shielding layer 420 may be formed of a chromium (Cr) layer.

Referring to FIG. 3B, the light-shielding layer 420 is patterned to form a first light-shielding pattern 421 on the blank region and a second light-shielding pattern 423 on the grating region C. The first and second light-shielding patterns 421, 423 can be patterned, for example, using a photolithography/etching technique or an electron beam scanning technique.

The first light-shielding pattern 421 is formed of a single pattern covering the blank region A of the transparent substrate 410, and the second light-shielding pattern 423 is formed of a plurality of parallel line patterns on the grating region C of the transparent substrate 410. As a result, line-shaped openings 425 exposing the transparent substrate 410 between the line patterns 423 are formed after the photolithography. In one exemplary embodiment, the width of each line pattern and the distance between two neighboring line patterns are formed constant.

Referring to FIG. 3C, the transparent substrate 410 is etched using the first and the second light-shielding patterns 421, 423 as an etch mask to form trench lines 430 corresponding to the openings 425 shown in FIG. 3B in the grating region C. Then, the first and the second light-shielding patterns 421, 423 are removed.

Figure 4:
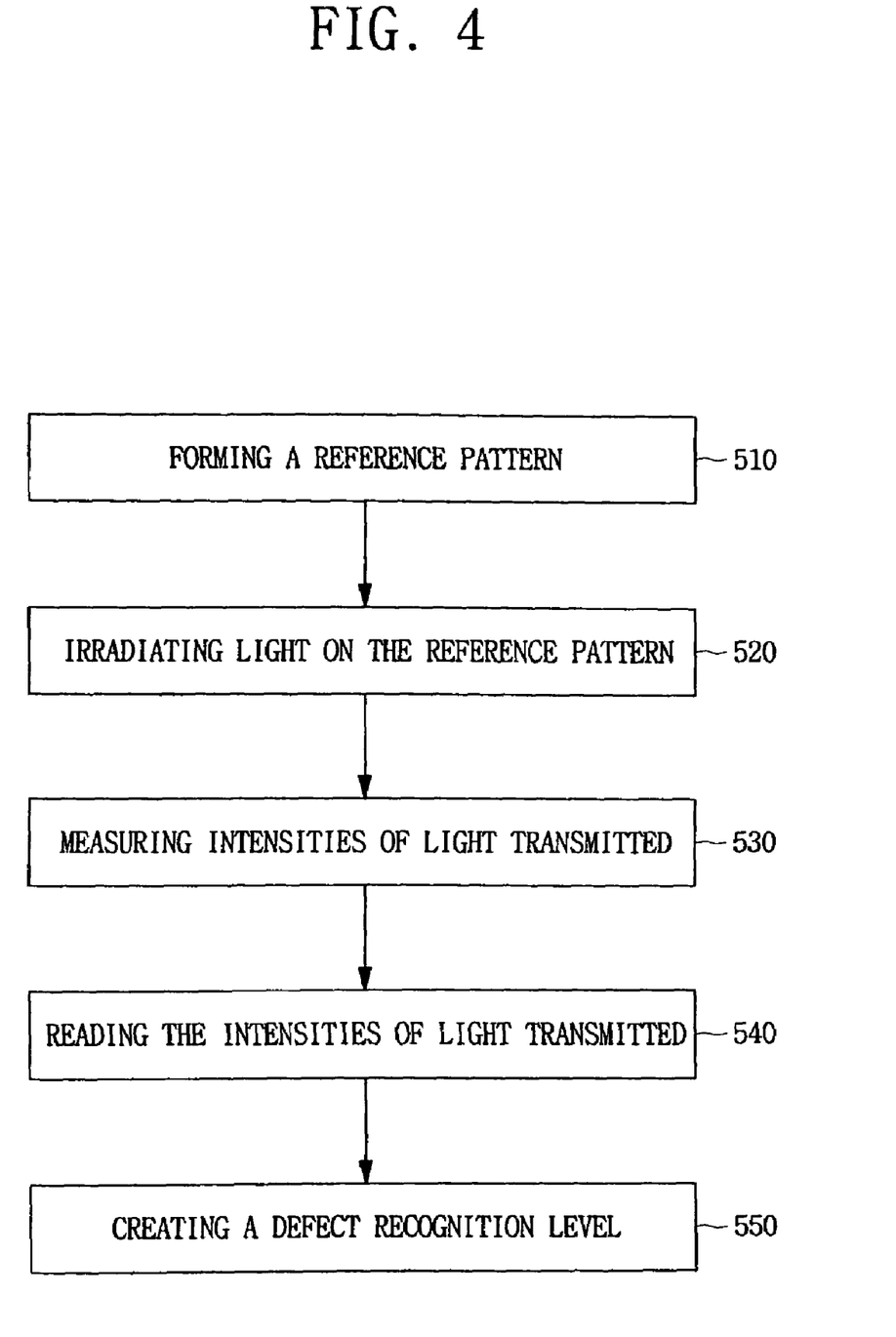
FIG. 4 is a flow diagram illustrating a method of creating a defect recognition level according to an exemplary embodiment of the present invention.

FIG. 4 is a flow diagram illustrating a method of creating a defect recognition level 300 using a reference pattern according to an embodiment of the present invention. Referring to FIG. 4, a reference pattern 410 (shown in FIG. 3C) is formed on a photomask as described in reference to FIGS. 3A to 3C (step 510). The photomask having the reference pattern 410 is loaded into a known defect inspection device (not shown), and light is irradiated on the photomask to be transmitted to the reference pattern 410 (step 520).

The light has a wavelength such as about 365 nm or about 248 nm. Alternatively, a wavelength shorter than about 248 nm can be used when integration of a semiconductor device increases. The light is irradiated on the blank region A and the grating region C shown in FIG. 3C. Then, intensities of light transmitted to the blank region A and the grating region C in the reference pattern are measured. (step 530)

The intensities of light measured in step 530 are to be read with a known measuring device (step 540). Then, the intensities of light transmitted to the blank region A and the grating region C in the reference pattern are normalized. In one exemplary embodiment, the intensity of light transmitted to the blank region A is normalized to be a standard intensity value of "1", and the intensity of light transmitted to the grating region C is normalized with respect to the standard intensity value of "1".

A defect recognition level 300 (shown in FIG. 2E) is provided to the defect inspection device (not shown) based on the normalized intensity values of light transmitted to the blank region A and the grating region C (step 550). The defect recognition level 300 is determined as a level between the normalized intensity values of light transmitted to the blank region A and the grating region C. In one exemplary embodiment, the defect recognition level may be determined as a middle value between the normalized intensity values of light transmitted to the blank region A and the normalized intensity values of light transmitted to the grating region C.

Figure 5:
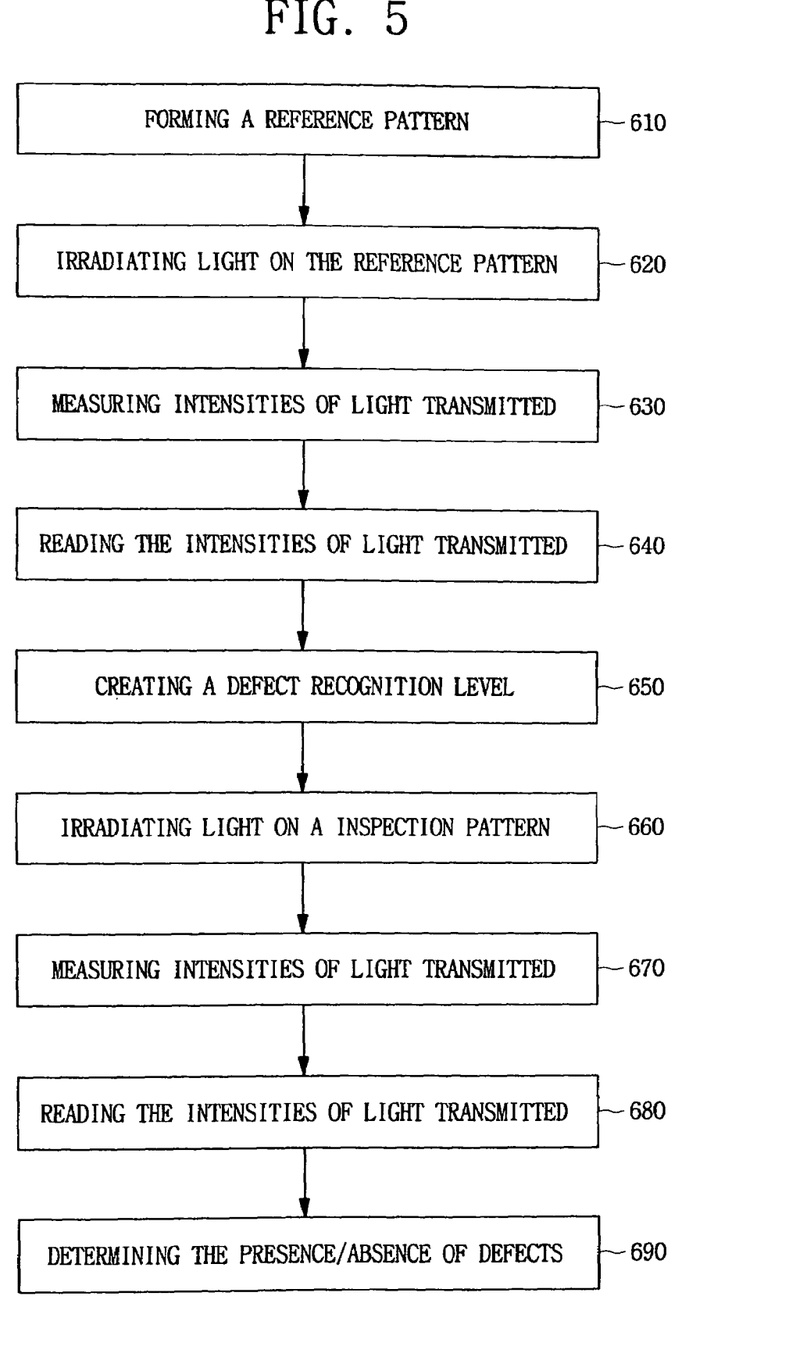
FIG. 5 is a flow diagram illustrating a method of inspecting defects on a photomask according to an exemplary embodiment of the present invention.

FIG. 5 is a flow diagram illustrating a method of inspecting defects on a photomask using a reference pattern according to an exemplary embodiment of the present invention. Referring to FIG. 5, a defect recognition level is provided to a known defect inspection device as explained in reference to FIG. 4 (steps 510 to 550 in FIG. 4 are same as steps 610 to 650 in FIG. 5). After the defect recognition level 300 is created, light having an inspection wavelength such as about 365 nm or about 248 nm is irradiated on an inspection pattern of a photomask under a defect inspection (step 660).

In one exemplary embodiment, a reference pattern for creating a defect recognition level is formed in the photomask to be inspected. Then, the thickness of the transparent substrate in the blank region A of FIG. 2A of the reference pattern and the phase 0 degree region 210 of FIG. 2D of the inspection pattern is identical. Thus, a more accurate inspection result can be obtained because an identical substrate thickness of the reference pattern and the inspection pattern is used. Furthermore, if the reference pattern is formed in the photomask to be inspected, it is sufficient to change locations of light irradiation without replacement of the photomask. Alternatively, if an inspection pattern and a reference pattern are formed in two different photomasks, the two different photomasks are irradiated separately.

While light is irradiated, intensity of light transmitted to the inspection pattern is measured (step 670). If an alternating phase shift photomask (for example, a photomask shown in FIG. 2D) is used, intensities of light transmitted to a phase 0 degree region, a light shielding region, and a phase shift region are measured. If a Cr-less mask (CLM) is used, intensities of light transmitted to a phase 0 degree region and a phase shift region are measured.

The measured intensities of light are read (step 680). If an area in which the measured intensity of light is lower than the defect recognition level is recognized, there is a light shielding pattern. If an area in which the measured intensity of light is higher than the defect recognition level is recognized, there is no light-shielding pattern.

Whether there is a defect on the inspection pattern can be determined by comparing the reference data on the database and an inspected result (step 690). Defects can be inspected by forming two identical inspection patterns on one photomask and comparing the inspection results for the two identical patterns. Then, an inspection result for one inspection pattern will be used as the reference data for inspecting defects on the other inspection pattern on the photomask.

After comparing the inspection result with the reference data, if a light-shielding pattern (which does not exist in the reference data) exists on the inspection pattern, such a light-shielding pattern is determined as a defect.

Figure 6A:
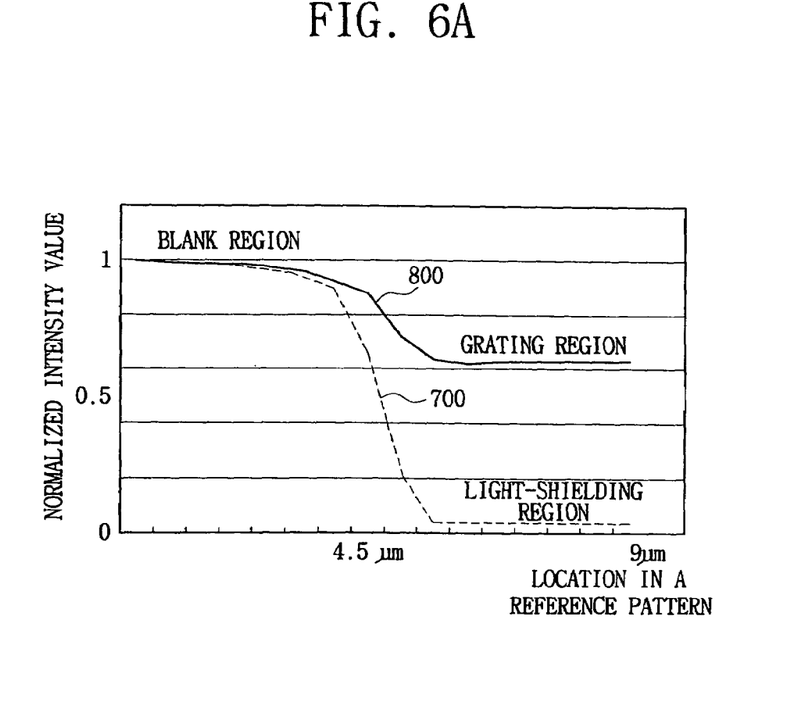
FIG. 6A is a graph explaining differences between a conventional defect recognition level and a defect recognition level according to an exemplary embodiment of the present invention.

FIG. 6A is a graph explaining differences between the conventional defect recognition level and the defect recognition level according to an exemplary embodiment of the present invention. A transparent quartz substrate and a chromium light-shielding layer are used. Trench lines of the grating region are formed to have a depth, which creates 180 degrees of phase difference with respect to the quartz substrate at about 365 nm wavelength light. The trench lines of the grating region have about 200 nm of a width of each line pattern and about 200 nm of a distance between two neighboring trench lines.

Referring to FIG. 6A, a graph of normalized intensity values of light 700, indicated by a dotted line, is obtained by irradiating about 365 nm wavelength light to the conventional reference pattern such as the blank region A shown in FIG. 1A and the light-shielding region B shown in FIG. 1A. Intensities of light transmitted to the blank region A of FIG. 1A and the light-shielding region B were measured and normalized.

A graph of normalized intensity value of light 800, indicated by a solid line, is obtained by irradiating about 365 nm wavelength light to the reference pattern such as the blank region A shown in FIG. 2A and the grating region C shown in FIG. 2A according to an embodiment of the present invention. Intensities of light transmitted to the blank region A and the grating region B are measured and normalized.

Because patterns for the conventional blank region A shown in FIG. 1A and the blank region A shown in FIG. 2A according to an embodiment of the present invention are identical, the intensities of light transmitted to each blank region show the same intensity value. The normalized intensity value of light with respect to both of the blank region A shown in FIG. 1A and FIG. 2A is determined as a standard intensity value of "1". Intensities of light transmitted to the light-shielding region B shown in FIG. 1A and the grating region C shown in FIG. 2A are indicated by normalized intensity values of light, respectively.

As shown in FIG. 6A, the normalized intensity value of light transmitted to the grating region C shown in FIG. 2A is higher than the normalized intensity value of light transmitted to the light-shielding region B shown in FIG. 1A. The normalized intensity values of light transmitted to the grating region C is even higher than the middle value between normalized intensity values of light transmitted to the light-shielding region B and the blank region A.

Therefore, a defect recognition level by using the reference pattern 300 according to an exemplary embodiment of the present invention has a higher normalized intensity values than the conventional defect recognition level 30.

Figure 6B:
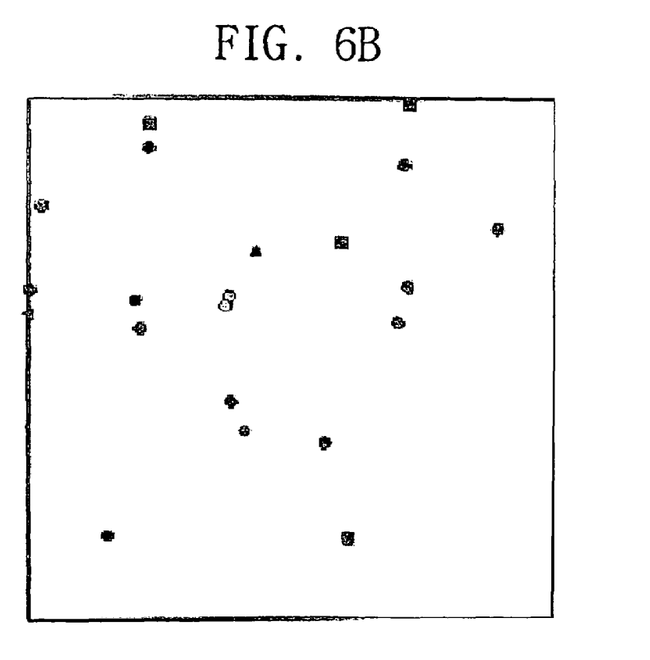
FIGS. 6B and 6C are maps showing defect distributions on a photomask measured using a conventional defect recognition level and a defect recognition level according to an exemplary embodiment of the present invention, respectively.
Figure 6C:
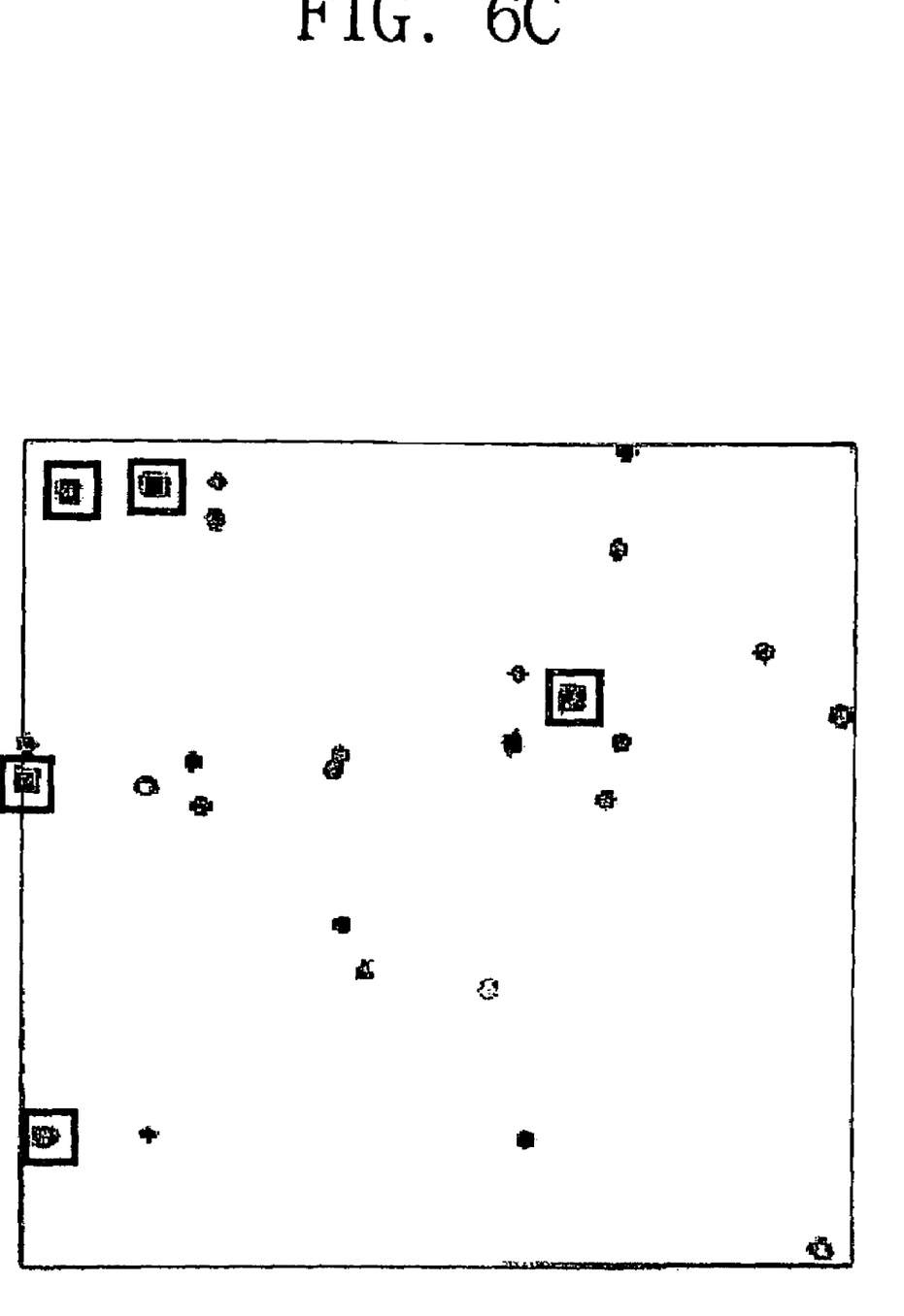

FIG. 6B and FIG. 6C are maps showing defects on a same photomask detected by using the conventional defect recognition level and the defect recognition level according to an exemplary embodiment of the present invention, respectively, as shown in FIG. 6A. Referring to FIGS. 6B and 6C, more defects are detected when the defect recognition level according to an embodiment of the present invention is used rather than the conventional defect recognition level is used. For example, defects surrounded by rectangles are transparent defects observed by a known optical microscope.

Although the exemplary embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention as defined by the appended claims.

What is claimed is:

1. A method of forming a reference pattern for creating a defect recognition level, comprising:

forming a light-shielding layer on a transparent substrate;
patterning the light-shielding layer to form a first light-shielding pattern and a second light-shielding pattern adjacent to the first light-shielding pattern, the first light-shielding pattern being formed of a single pattern covering the overall surface of a portion of the transparent substrate, and the second light-shielding pattern being formed of a plurality of parallel line patterns to form line-shaped openings exposing the transparent substrate, wherein each parallel line pattern has a length that is substantially longer than a width;
etching the transparent substrate using the first and the second light-shielding patterns as an etch mask to form trench lines corresponding to the line-shaped openings, the trench lines having a depth such that light transmitted therethrough has a phase difference with respect to light transmitted through the transparent substrate between the trench lines; and
removing the first and the second light-shielding patterns to form a blank region corresponding to the first light-shielding pattern, and a grating region corresponding to the second light-shielding pattern and the line-shaped openings,
wherein the blank region and the grating region are used for creating a transparent defect recognition level,
wherein intensity of light transmitted through the grating region is lower than intensity of light transmitted through the blank region due to interference between the light transmitted through the trench lines and the light transmitted through the transparent substrate between the trench lines, which have the phase difference,
wherein the trench lines have a depth such that light transmitted thereto has 180 degrees of phase difference with respect to light transmitted through the transparent substrate between the trench lines.

2. The method of claim 1, wherein the reference pattern is formed on a photomask.

3. The method of claim 1, wherein the light-shielding layer is formed of a chromium (Cr) layer.

4. The method of claim 1, wherein the plurality of parallel line patterns are formed to have an identical width and an identical depth.

5. The method of claim 1, wherein distances between the plurality of parallel line patterns are formed to be identical.

6. The method of claim 4, wherein width of the plurality of line patterns is formed to be identical to a distance between the plurality of parallel line patterns.

7. The method of claim 6, wherein the width of the plurality of the line patterns and the distance between the plurality of the line patterns is less than about 300 nm.

8. The method of claim 1, wherein a size of the blank region and a size of the grating region is large enough not to be affected by interference of light transmitted through neighboring patterns of the blank region and the grating region.

9. A method of creating a defect recognition level, comprising:

fabricating a reference pattern on a transparent substrate, the reference pattern including a blank region and a grating region formed adjacent to the blank region, wherein the grating region includes a plurality of trench lines formed in the transparent substrate;
irradiating light on the reference pattern;
measuring intensities of light transmitted through the reference pattern; and selecting a transparent defect recognition level between intensity of light transmitted through the blank region of the reference pattern and intensity of light transmitted through the grating region of the reference pattern.

10. The method of claim 9, wherein the reference pattern is formed on a photomask.

11. The method of claim 9, wherein the plurality of trench lines are formed to have an identical width and an identical depth.

12. The method of claim 11, wherein distances between the plurality of trench lines are formed to be identical.

13. The method of claim 9, wherein the trench lines have a depth such that light transmitted through has 180 degrees of phase difference with respect to light transmitted to the transparent substrate between the trench lines.

14. The method of claim 11, wherein the width of the plurality of trench lines is formed to be identical to a distance between the plurality of trench lines.

15. The method of claim 14, wherein width of the plurality of the trench lines and the distance between the plurality of the trench lines is less than about 300 nm.

16. The method of claim 9, wherein wavelength of the irradiated light transmitted through the reference pattern is about 365 nm or about 248 nm.

17. The method of claim 9, wherein the transparent defect recognition level is a middle value between the intensity of light transmitted through the blank region and the intensity of light transmitted through the grating region.

18. A method of inspecting defects, comprising:
fabricating a reference pattern on a transparent substrate, the reference pattern including a blank region on the transparent substrate, and a grating region formed adjacent to the blank region and having a plurality of trench lines formed in the grating region;
irradiating light on the reference pattern;
measuring intensities of light transmitted through the reference pattern;
selecting a transparent defect recognition level between the intensity of light transmitted through the blank region of the reference pattern and the intensity of light transmitted to the grating region of the reference pattern;
irradiating light on an inspection pattern under a transparent defect inspection;
measuring intensities of light transmitted through the inspection pattern; and
reading the measured intensities of light and determining a presence or an absence of transparent defects.

19. The method of claim 18, wherein the reference pattern is formed on a photomask.

20. The method of claim 18, wherein wavelength of the irradiated light transmitted through the reference pattern is about 365 nm or about 248 nm.

21. The method of claim 18, wherein the plurality of trench lines are formed to have an identical width and an identical depth.

22. The method of claim 21, wherein distances between the plurality of trench lines are formed to be identical.

23. The method of claim 18, wherein the trench lines have a depth such that light transmitted therethrough has 180 degrees of phase difference with respect to light transmitted through the transparent substrate between the trench lines.

24. The method of claim 22, wherein width of the plurality of trench lines is formed to be identical to the distance between the plurality of trench lines.

25. The method of claim 24, wherein the width of the plurality of the trench lines and the distance between the plurality of the trench lines is less than about 300 nm.

26. The method of claim 18, wherein the level is a middle value between the intensity of light transmitted through the blank region and the intensity of light transmitted through the grating region.

27. The method of claim 1, wherein a width of each trench line is substantially identical to a depth of each trench line.

28. The method of claim 9, wherein a width of each trench line is substantially identical to a depth of each trench line.

29. The method of claim 18, wherein a width of each trench line is substantially identical to a depth of each trench line.

30. The method of claim 1, wherein the size of the blank region and the size of the grating region are substantially the same.

31. The method of claim 9, wherein the size of the blank region and the size of the grating region are substantially the same.

32. The method of claim 18, wherein the size of the blank region and the size of the grating region are substantially the same.

* * * * *